United States Patent [19]

Bauer et al.

[11] Patent Number: 4,558,070
[45] Date of Patent: Dec. 10, 1985

[54] ACID SALTS OF VALPROIC ACID

[75] Inventors: John F. Bauer, Wilmette, Ill.; Douglas M. Shada, Kenosha, Wis.

[73] Assignee: Abbott Laboratories, North Chicago, Ill.

[21] Appl. No.: 545,710

[22] Filed: Oct. 26, 1983

[51] Int. Cl.[4] .................... A61K 31/19; C07C 53/128
[52] U.S. Cl. .................................... 514/557; 562/606
[58] Field of Search .................. 562/606; 424/317; 514/557

[56] References Cited

FOREIGN PATENT DOCUMENTS 1074978 10/1954 France .................. 562/606
2442M 4/1964 France .................. 562/606

Primary Examiner—Vivian Garner
Attorney, Agent, or Firm—Steven F. Weinstock; Martin L. Katz

[57] ABSTRACT

Acid salts of valproic acid having the structure:

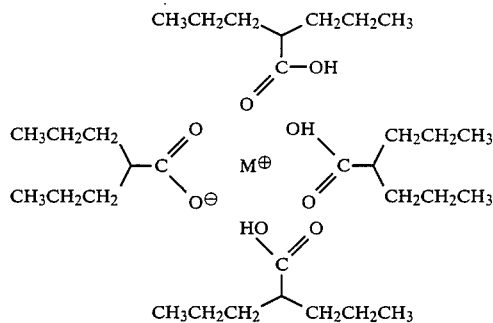

wherein M is potassium, cesium or rubidium. The salts of the invention are useful in the treatment of epileptic seizures, and can be conveniently formulated into oral dosage forms.

5 Claims, No Drawings

ACID SALTS OF VALPROIC ACID

This invention relates to valproate salts, and more particularly to certain alkali metal salts of valproic acid having improved stability.

Valproic acid or 2-propylpentanoic acid has come into wide-spread use in the treatment of epileptic seizures or convulsions. Most commonly used are valproic acid and its sodium salt; the acid is a liquid while the sodium salt is a hygroscopic solid characterized by poor stability. As a result, both have limited utility in the preparation of oral dosage forms.

Significant improvements in the forms of valproic acid-salts have been achieved as described in copending application Ser. No. (545,719), filed concurrently herewith, the disclosure of which is incorporated herein by reference. As described in that application, it has been found that highly stable, non-hygroscopic compounds derived from valproic acid can be prepared from equimolar amounts of (a) valproic acid or diethylacetic acid and (b) a valproate salt of sodium or calcium.

It has been discovered that compounds thus produced are in the nature of an oligomer. For example, the compound formed from valproic acid and sodium valproate has the structure:

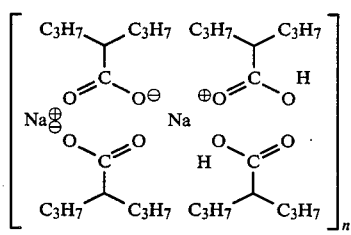

The oligomer contains from about 2 to 20, preferably from about 4 to 12 and most preferably about 8 of the repeating units.

A comparison of infrared spectra and X-ray diffraction patterns of sodium valproate, valproic acid and the sodium complex reveal that the above complex (I) is a chemical entity and not a mixture of the two precursors. Without limitation as to theory, the outer shell of electrons of the sodium atom is filled by coordination to the oxygen atoms of both valproic acid and valproate ions, resulting in a stable complex in which the sodium ion is completely surrounded by oxygen.

As described in the foregoing application, attempts to produce the corresponding potassium complex (as well as other alkali and alkaline earth metals) were unsuccessful. Specifically, 2 moles of valproic acid were reacted with one mole of KOH, and the product was highly hygroscopic.

That can be explained by the same type analysis in that, in the case of potassium, twelve electrons are necessary to fill its 4s and 3d orbitals. Since 2 moles of valproic acid do not completely fill the outer electron shell of potassium, supplying only 8 of the twelve necessary electrons, the remaining 4 electrons must come from 2 molecules of water. That, as those skilled in the art will appreciate, means that 2 molecules of water must be present to complete the coordination sphere, thus rendering the complex hygroscopic. That hygroscopic complex may be illustrated as follows:

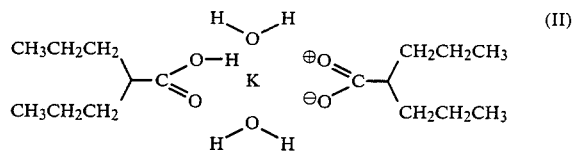

Cesium and rubidium both have atomic structures similar to potassium in that both have unoccupied d orbitals. Thus, cesium and rubidium form hygroscopic complexes like sodium.

It is accordingly an object of the present invention to provide valproic acid salts of potassium, rubidium and cesium which are stable and non-hygroscopic.

It is another object of the present invention to provide acid salts of potassium, cesium and rubidium which can be formulated into solid, crystalline stable dosage forms.

The concepts of the invention reside in a discovery that a stable complex between valproic acid and potassium, cesium and rubidium may be formed by combining 4 moles of valproic acid with 1 mole of the alkali metal ion. Without limiting the present invention as to theory, the presence of 4 valproic acid groups for each alkali metal cation completely fills the 3d orbitals of the alkali metal atom to form a stable atomic orbital. It is critical to the practice of the invention that the molar ratio of valproic acid to alkali metal ion be 4:1. If less than 4 moles of valproic acid are combined with 1 mole of the alkali metal ion, the 3d orbital of the alkali metal is not filled and can only be filled by the complex taking on water, and hence becoming hygroscopic.

The compounds of the present invention are distinct chemical entities, crystalline in nature and having well defined physical and chemical properties. Without limiting the invention as to theory, it is believed that the complexes thus formed have the structure:

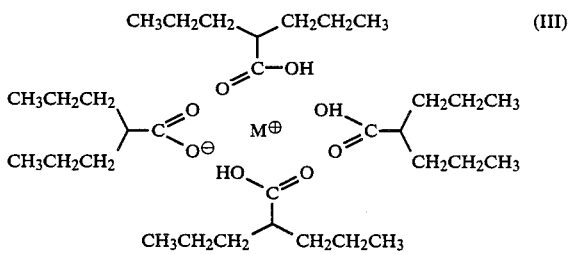

wherein M is a potassium, cesium or rubidium cation. These compounds have the advantage over the corresponding sodium salt in that they provide 4 moles of valproic acid for each mole of alkali metal, as compared to the sodium salt which provides only 2 moles of valproic acid for each mole of alkali metal. Unlike the sodium salt, the salts of this invention are not polymeric.

The new salts of the present invention can be prepared by reacting one mole of the corresponding alkali metal hydroxide of potassium, cesium or rubidium with 4 moles of valproic acid in aqueous media, and then removing the water to recover the crystalline complex thus produced. As will be appreciated by those skilled, the inclusion of small amounts of other fatty acids such as diethylacetic acid does not materially alter the complex thus produced in that it simply replaces one or more moles of valproic acid with a biologically inactive acid.

The resulting complex is thus formed of one mole of the alkali metal valproate and three moles of valproic acid. Those salts are useful in the treatment of epileptic seizures or convulsions, and can conveniently be formulated in solid dosage forms, either alone or in combination with one or more pharmaceutically acceptable diluents in accordance with U.S. Pat. No. 3,325,361. Typical diluents or excipients include starch, talcum powder, lubricants, disintegrators, flavoring agents, coloring agents or the like.

When used herein in the treatment of epileptic seizures or convulsions, the compounds and compositions of the present invention should be administered in an amount of from 1 to 100 mg/kg body weight/day, preferably 16 to 64 mg/kg body weight/day of valproic acid.

Having described the basic concepts of the invention, reference is now made to the following examples which are provided by way of illustration, and not by way of limitation, of the practice of the invention.

EXAMPLE 1

This example illustrates the preparation of the potassium salt of valproic acid.

One mole of KOH (56.10 g) was dissolved in 100 ml of water in a 500 ml volumetric flask equipped with a stirrer and heating mantle. Four moles of valproic acid (576.84 g) were added and the resulting mixture stirred and heated to boiling.

The water was distilled off over a period of approximately 2 hours, and the residue in the flask solidified. That solid was isolated and dried by dissolving in hexane, drying over anhydrous sodium sulfate, filtering and then evaporating the hexane.

The compound obtained has a molecular weight of 615, having a melting point of 56.6° C. That is a substantially lower melting point than the corresponding sodium salt, thus confirming the monomer structure of the potassium salt.

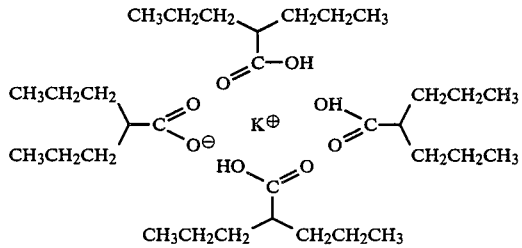

EXAMPLE 2

This example illustrates the preparation of the cesium salt.

Using the procedure of Example 1, one mole of CsOH (149.92 g) was reacted with 4 moles of valproic acid.

The product of the reaction was recovered as described in Example 1, and was found to be Cs valproate 0.3 valproic acid having the structure (III).

EXAMPLE 3

This example illustrates the preparation of the rubidium salt.

Using the proedure of Example 1, one mole of RbOH (102.49 g) was reacted with 4 moles of valproic acid.

The product of the reaction was recovered as described in Example 1, and was found to be Rb valproate 0.3 valproic acid having the structure (III).

It will be understood that various changes and modifications can be made in the details of procedure, formulation and use without departing from the spirit of the invention, especially as defined in the following claims.

We claim:
1. A compound of the formula M Valproate 0.3 Valproic Acid wherein M is an alkali metal ion selected from the group consisting of K, Cs and Rb.
2. A compound as defined in claim 1 wherein M is potassium.
3. An oral pharmaceutical dosage form for treating epileptic seizures or convulsions containing an effective amount of a compound of the formula: M Valproate 0.3 Valproic Acid wherein M is an alkali metal ion selected from the group consisting of K, Cs and Rb and a pharmaceutically acceptable diluent.
4. An oral dosage form as defined in claim 3 wherein M is potassium.
5. A method of treating epileptic seizures or convulsions which comprises administering to a patient in need of such treatment a therapeutically effective amount of a compound of the formula:

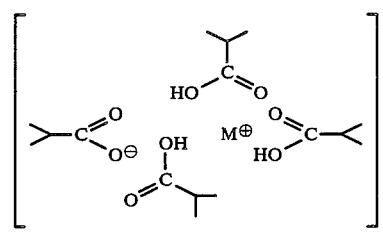

M Valproate 0.3 Valproic Acid, wherein M is an alkali metal ion selected from the group consisting of K, Cs and Rb.

* * * * *

UNITED STATES PATENT AND TRADEMARK OFFICE
CERTIFICATE OF CORRECTION

PATENT NO. : 4,558,070
DATED : December 10, 1985
INVENTOR(S) : John F. Bauer et al It is certified that error appears in the above—identified patent and that said Letters Patent is hereby corrected as shown below:

In The Specification:

Col. 2, line 5, delete

" 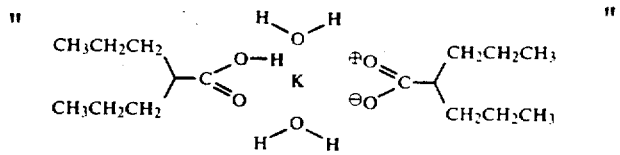 "

and insert

-- 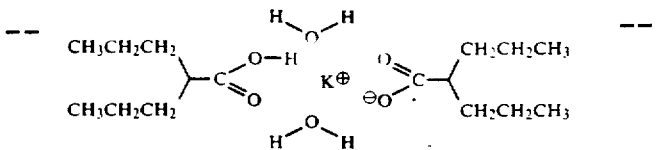 --

Col. 4, line 10, delete "0.3" and insert -- ·3 --.
Col. 4, line 19, delete "0.3" and insert -- ·3 --.

In The Claims:

Claim 1, line 1, delete "0.3" and insert -- ·3 --.
Claim 3, line 3, delete "0.3" and insert -- ·3 --.

UNITED STATES PATENT AND TRADEMARK OFFICE
CERTIFICATE OF CORRECTION

PATENT NO. : 4,558,070
DATED : December 10, 1985
INVENTOR(S) : John F. Bauer et al It is certified that error appears in the above-identified patent and that said Letters Patent is hereby corrected as shown below:

Claim 5, line 5, delete structure.
Claim 5, line 6, delete "0.3" and insert -- ˙3 --.

Signed and Sealed this

Twenty-fourth Day of February, 1987

Attest:

DONALD J. QUIGG

Attesting Officer

Commissioner of Patents and Trademarks